US009611187B2

(12) United States Patent
Gruetzner et al.

(10) Patent No.: US 9,611,187 B2
(45) Date of Patent: Apr. 4, 2017

(54) METHOD OF CARRYING OUT A CHEMICAL EQUILIBRIUM REACTION USING A PERMSELECTIVE MEMBRANE

(71) Applicant: MUW SCREENTEC Filter- und Praezisionstechnik aus Metall GmbH, Wittingen (DE)

(72) Inventors: Joerg Gruetzner, Schildow (DE); Dirk Martin, Erfurt (DE)

(73) Assignee: MUW SCREENTEC FILTER- UND PRAEZISIONSTECHNIK AUS METALL GMBH, Wittingen (DE)

( * ) Notice: Subject to any disclaimer, the term of this patent is extended or adjusted under 35 U.S.C. 154(b) by 0 days.

(21) Appl. No.: 14/970,681

(22) Filed: Dec. 16, 2015

(65) Prior Publication Data

US 2016/0176775 A1 Jun. 23, 2016

(30) Foreign Application Priority Data

Dec. 17, 2014 (DE) ........................ 10 2014 118 894

(51) Int. Cl.
*C07C 1/12* (2006.01)
*C07C 29/152* (2006.01)
*C07C 29/76* (2006.01)

(52) U.S. Cl.
CPC .............. *C07C 1/12* (2013.01); *C07C 29/152* (2013.01); *C07C 29/76* (2013.01); *C07C 2521/04* (2013.01); *C07C 2523/755* (2013.01)

(58) Field of Classification Search
CPC ......... C07C 29/152; C07C 29/76; C07C 1/12; C07C 9/04; C07C 2521/04; C07C 2523/755; B01D 69/145
See application file for complete search history.

(56) References Cited

U.S. PATENT DOCUMENTS

| 5,427,687 | A | 6/1995 | Blum et al. |
|---|---|---|---|
| 9,101,890 | B2 | 8/2015 | Tonkovich et al. |
| 2003/0101866 | A1 | 6/2003 | Noack |
| 2006/0159718 | A1 | 7/2006 | Rathenow et al. |
| 2009/0326279 | A1 | 12/2009 | Tonkovich et al. |
| 2015/0336074 | A1 | 11/2015 | Tonkovich et al. |

FOREIGN PATENT DOCUMENTS

| DE | 4019170 A1 | 12/1991 |
|---|---|---|
| DE | 10335131 A1 | 2/2005 |
| JP | 2007055970 | 3/2007 |
| WO | 2006127889 A2 | 11/2006 |

OTHER PUBLICATIONS

Ralston, J. www.pennenergy.com/index/power /display/ 0723256773/articles/pennenergy/ugc/renewable/the-sabatier-reaction.html Mar. 2010.
Wang, H., et al., "Effects of Water Vapor on Gas Permeation and Separation Properties of MFI Zeolite Membranes at High Temperatures", AIChE Journal Jan. 2012 vol. 58, No. 1, pp. 153-162.
Sano, T. et al., Separation of ethanol/water mixture by silicalite membrane on pervaporation, Journal of Membrane Science 95(3), pp. 221-228 (1994).
Hamzah, A., et al., "Pervaporation through NaA Zeolite Membranes—A Review", The Third Basic Science International Conference 2013, pp. CO3-1 to CO3-5.
Damle, A. S., et al., Thermal and Chemical Degradation of Inorganic Membrane Materials, Technical Report, May 1995 87 pages.
Gu, Y., et al.: Hydrothermally stable silica—alumina composite membranes for hydrogen separation, Journal of Membrane Science 310 (1-2): 28-37 (2008).
Bettermann, I., et al., "Membranverfahren zur Auftrennung von gasfoermigen und fluessigen Stoffgemischen", www.analytik-news. de, Aug. 19, 2010, pp. 1-17.
Caro, J., et al., "Why is it so extremely difficult to prepare shape-selective Al-rich zeolite membranes like LTA and FAU for gas separation?", Separation and Purification Technology 66(1), 143-147 (2009).
Ohya, H., et al. "Methanation of carbon dioxide by using membrane reactor integrated with water vapor permselective membrane and its analysis", Journal of Membrane Science 131, 237-247 (1997).
Hwang, H. T., et al. "A membrane-based reactive separation system for CO2 removal in a life support system", Journal of Membrane Science 315 (1-2), 116-124 (2008).
Habazaki, H., et al. "Co-methanation of carbon monoxide and carbon dioxide on supported nickel and cobalt catalysts prepared from amorphous alloys", Applied Catalysis A: General 172, 131-140 (1998).
Waldburger, R., "Membraneinsatz bei chemischen Produktionsverfahren", Schweizer Ingenieur und Architekt 112(42), 1994, pp. 839-847.
Krippner, W., Untersuchung und Bewertung der Möglichkeiten zur Methanisierung des CO2-Anteils fermentativer Biogase, Bachelor Thesis, Berlin 2012.

*Primary Examiner* — Jafar Parsa
(74) *Attorney, Agent, or Firm* — Abel Law Group, LLP

(57) ABSTRACT

The invention relates to a method of carrying out a chemical equilibrium reaction using a permselective membrane, wherein quantitative proportions of at least one product obtained in the reaction are separated and removed from the reaction through the action of the permselective membrane. The chemical equilibrium reaction is carried out in the presence of a water-containing gas mixture, and a permselective membrane made from a material having a porous structure with mean pore sizes of less than 0.45 nm (4.5 Å), which material is hydrophobic at least on the free surfaces thereof is used.

20 Claims, No Drawings

METHOD OF CARRYING OUT A CHEMICAL EQUILIBRIUM REACTION USING A PERMSELECTIVE MEMBRANE

CROSS-REFERENCE TO RELATED APPLICATIONS

The present application claims priority under 35 U.S.C. §119 of German Patent Application No. 102014118894.2, filed Dec. 17, 2014, the entire disclosure of which is expressly incorporated by reference herein.

BACKGROUND OF THE INVENTION

1. Field of the Invention

The present invention is directed to a method for carrying out chemical equilibrium reactions using a permselective membrane. The invention is directed particularly to a method for converting carbon dioxide and hydrogen using a carbon membrane.

2. Discussion of Background Information

The conversion of hydrogen with carbon dioxide is pursued essentially for two reasons. On the one hand, hydrogen is increasingly produced by electrolysis for buffering grid fluctuations from the increasing proportion of fluctuating flow from regenerative sources ("power to gas"). The storage and distribution of hydrogen can be carried out directly in the natural gas network in small proportions. Storage and distribution would be possible on a much larger scale by converting with carbon dioxide to methane. The second reason relates to the chemical bonding and utilization of carbon dioxide and, therefore, has considerable advantages in technical respects relating to environment and climate.

In the Sabatier reaction, which is a chemical equilibrium reaction and is known to the person skilled in the art, carbon dioxide ($CO_2$) and hydrogen ($H_2$) (reactants) are converted to methane ($CH_4$) and water ($H_2O$) (products). The Sabatier reaction is usually carried out at pressures of ~1 . . . 3 bara (absolute pressure; bar, absolute), also infrequently at higher pressures of up to 15 bara, and in a temperature range of around 200 to 450° C. Known suitable catalysts for this reaction are, for example, nickel, ruthenium, rhodium and cobalt which are usually arranged on an oxide support such as $SiO_2$, $TiO_2$, MgO, $Al_2O_3$ and $La_2O_3$ as is described, for example, in Ohya et al., 1997: Methanation of carbon dioxide by using membrane reactor integrated with water vapor permselective membrane and its analysis, *Journal of Membrane Science* 131 (1-2), the entire disclosure of which is incorporated by reference herein. The most successful combination at the present time is that of 0.5% Ru over $TiO_2$. Depending on the catalyst, high $CO_2$ conversions and $CH_4$ yields are achieved at temperatures of ~300 . . . 350° C. (John Ralston (www.pennenergy.com/index/power/display/0723256773/articles/pennenergy/ugc/renewable/the-sabatier-reaction.html).

The Sabatier reaction is a very demanding reaction because it is highly exothermic and, depending on the degree of dilution with inert gases, leads to temperatures above 600° C. after the addition of the reactants. At this temperature level, not only are some catalysts destroyed—for example, active sites are lost, e.g., by sintering of Ni particles in the nm range—but the reaction equilibrium also shifts in the reactant direction. On the other hand, temperatures that are too low result in kinetic limiting of the reaction and amount of the desired products.

Various publications have already addressed the use of membranes. Accordingly, the use of a membrane of twenty-coat hydrophilic porous glass on a ceramic support results at best in an 18-percent increase in $CO_2$ conversion (at 300° C., 0.2 MPa and space velocity=0.0308 s$^{-1}$) (Ohya et al.). The conversion increase is noteworthy, but the space velocity ranges far below required industrial ranges of at least 3 s$^{-1}$. Moreover, concentration of carbon dioxide by the membranes precedes the actual Sabatier reaction (Hwang et al. 2008: A membrane-based reactive separation system for $CO_2$ removal in a life support system, *Journal of Membrane Science* 315 (1-2): 116-124, the entire disclosure of which is incorporated by reference herein Calculations show synergistic positive effects for the reaction in this case. However, further process concepts are also possible. The hydrogen conversion under consideration here can be increased by approximately 90% to up to 99% over the procedure of reaction with two reactors connected in tandem with intermediate removal of the reaction water (Habazaki et al. 1998: Co-methanation of carbon monoxide and carbon dioxide on supported nickel and cobalt catalysts prepared from amorphous alloys, *Applied Catalysis A: General* 172 (1): 131-140, the entire disclosure of which is incorporated by reference herein). However, the separation of the products methane and water is a mandatory prerequisite for possible injection into the natural gas grid.

Since the Sabatier reaction is an exothermic equilibrium reaction, it is limited with respect to yield as reaction temperature or process temperature increases. Removal of a reaction product directly from the reaction in the process causes an increase in the driving force for product formation. A suitable water-separating membrane achieves precisely this in that the reaction product water is separated directly in the process. Accordingly, yield is increased compared to the process without membrane. Further, by separating out the reaction water, subsequent drying of the methane to ensure feed quality is superfluous and this process step can be omitted.

Methanol can be produced, for example, from a syngas of carbon monoxide and hydrogen. Particularly in the production of methanol from carbon dioxide and hydrogen as reactants and methanol and water as products of a chemical equilibrium reaction, the yield can likewise be improved when it is possible to separate the water on the product side.

In order to separate water from gas mixtures at elevated temperatures, it is conventional to use hydrophilic membranes. These hydrophilic membranes are, in particular, $SiO_2$ membranes and zeolite A membranes (Wang et al., 2011: "Effects of water vapor on gas permeation and separation properties of MFI zeolite membranes at high temperatures, *AIChE Journal* 58(1); Sano et al., 1994: "Separation of ethanol/water mixture by silicate membrane on pervaporation, *Journal of Membrane Science* 95 (3); Hamzah et al., 2013: "Pervaporation through NaA zeolite membranes—A review", *The Third Basic Science International Conference* 2013, the entire disclosures of which are incorporated by reference herein).

The preferred application is dewatering and drying of solvent vapors. However, the use of these membranes in the Sabatier reaction for separating water from a mixture with hydrogen, carbon dioxide and methane shows an insufficient selectivity and, further, an insufficient stability of the materials under the required conditions for the Sabatier reaction. Under reducing conditions such as are present in the Sabatier reaction, $SiO_2$ membranes are subject to thermal degradation above 100° C. (Damle at al., 1995: "Thermal and chemical degradation of inorganic membrane materials", *Technical Report*; Gu et al.: "Hydrothermally stable silica-alumina composite membranes for hydrogen separation", *Journal of Membrane Science* 310 (1-2): 28-37), and zeolite A membranes have insufficient stability in acidic environments and sometimes limited thermal stability (Hamzah et al., 2013: Pervaporation through NaA zeolite membranes—A review", *The Third Basic Science International Conference*; C03; Caro et al., 2009: Why is it so extremely difficult to prepare shapeselective Al-rich zeolite membranes like LTA and FAU for gas separation?, *Separation and Purification Technology* 66(1): 143-147, the entire disclosures of which are incorporated by reference herein) such as those occurring in combinations of $H_2O$ and $CO_2$.

It would be advantageous to have available a method of carrying out equilibrium reactions in which water is separated on the reaction product side and an improved yield of reaction products is achieved.

SUMMARY OF THE INVENTION

The present invention provides a method of carrying out a chemical equilibrium reaction in which carbon dioxide and hydrogen are converted using a permselective membrane, wherein quantitative proportions of at least one product obtained in the reaction are separated and removed from the reaction through the action of the permselective membrane. The method is characterized in that a permselective membrane is used which is made from a material having a porous structure with mean pore sizes of less than 0.45 nm (4.5 Å), and the material thereof is hydrophobic at least on the free surfaces thereof. A material is considered hydrophobic when contact angles of 85° or more are measured at a water drop applied to it.

The chemical equilibrium reaction is carried out in the presence of a water-containing gas mixture. A water-containing gas mixture is obtained, for example, by the products methane and water of the Sabatier reaction. Because of the high temperatures at which this equilibrium reaction takes place, the water is in the form of water vapor. As understood within the meaning of the present description, a mixture of methane and water vapor is a gas mixture, particularly a water-containing gas mixture.

The core of the invention is the use of an organic membrane comprising substantially carbon and/or hydrocarbons. The permselective membrane (hereinafter also referred to as membrane for brevity) is preferably a carbon membrane.

In this respect, it has been shown surprisingly that water is selectively separated from the aforementioned mixture of products through a carbon membrane of the type mentioned above under the conditions of the equilibrium reaction (hereinafter also referred to as reaction for brevity).

The membrane can be arranged, for example, on ceramic elements of various length and diameter which function as supports. The membranes can be on an inner side and/or on an outer side of the supports. On the inner side and/or on the outer side of the supports, the supports can have intermediate layers with decreasing pore size over which the membrane can be arranged. For example, supports have a length of from 10 to 2000 mm, for example, from 105 mm to 250 mm. The supports can be partially or completely coated with the membrane on the inner side and/or outer side of the support. Further, membranes can be produced on supports of any shape with a length of, for example, from 10 to 2000 mm, for example, about 500 mm. As additional step for outer coating, ceramic supports which are closed on one side can be produced and the membrane can also be applied to the outer side thereof.

When partially coated supports are used, it must be ensured, for example, by means of a constructional step that a separation of the water takes place only over the regions of the support that are coated by the membrane.

Therefore, in a preferred embodiment of the method according to the invention, the permselective membrane is a carbon membrane, the structure of the material is graphite-like and is formed by layers of the material, the structure is formed by at least one series of layers, wherein the layers are arranged in planes, and there is a mean spacing of the layers of less than 0.45 nm (4.5 Å) between adjacent layers, and the series of layers is turbostratically disordered.

In a very favorable embodiment of the method according to the invention, a membrane is used in which at least one metal-containing catalyst is arranged on a surface of the permselective membrane. As used herein, the expression "arranged" means that the catalyst is connected to the membrane or directly contacts it. The catalyst is preferably in the form of particles which are bonded to a surface of the membrane and/or lies at or on the latter as bulk material.

The catalyst can also be provided as a coating on the membrane or on portions of the membrane.

Catalysts can be metal-containing catalysts from a group comprising the metals ruthenium, nickel, cobalt, rhodium, platinum and palladium, or alloys thereof. The expression "metal-containing catalysts" also includes metallic catalysts.

It is very advantageous for conducting the reaction and for a high product yield when the chemical equilibrium reaction is carried out with a hydrogen surplus with respect to the stoichiometric use of molecular hydrogen ($H_2$). The hydrogen surplus can amount to 2.5% with respect to the stoichiometric use of molecular hydrogen. An unwanted formation of coke can be prevented to a great extent through a surplus of hydrogen.

Advantageously, gases such as biogas, sewage gas, biomethane, molecular hydrogen-containing carbon dioxide streams, molecular hydrogen-releasing electrolysis, hydrogen streams or combinations thereof can be used as sources of the molecular hydrogen.

In this respect, it is advantageous for purposes of an efficient implementation of the method when the sources of molecular hydrogen are process-treated before using in the method according to the invention. For example, they can be reduced and desulfurized such that they contain ≤1 ppm of oxygen ($O_2$) and sulfur (S) and feed quality is ensured.

The chemical equilibrium reaction is preferably either a Sabatier reaction or a methanol production reaction.

The method according to the invention, particularly the Sabatier reaction, is preferably carried out at a pressure from 1 up to and including 100 bar, e.g., at about 5, 75, 100 bar, and at a temperature of from 150 up to and including 600° C., e.g., at about 400, 500° C.

It has proven favorable that the Sabatier reaction is carried out at a pressure of from 10 to 20 bar and at a temperature of from 250 to 450° C. In particular, the Sabatier reaction can be carried out efficiently at a pressure of about 20 bar and at a temperature of about 300° C.

If the chemical equilibrium reaction is a methanol production reaction, it is preferably carried out at a pressure of from 80 bar up to and including 250 bar and at a temperature of from 150° C. up to and including 400° C.

Methanol ($CH_3OH$), as the simplest representative of the substance group of alcohols, is one of the most produced organic chemicals and serves as a starting material for many other chemical products (e.g., formaldehyde, formic acid, etc.). The technical production is carried out chiefly through a reaction of CO and $H_2$ over a catalyst. Depending upon the reaction pressures, the methods for methanol production are divided into high-pressure methods (250-350 bar, ~370° C.), intermediate-pressure methods (100-250 bar, ~220-300° C.), and low-pressure methods (50-100 bar, 200-300° C.). Owing to economic drawbacks, the high-pressure method is no longer applied at present. Copper-zinc catalysts on aluminum oxide are used extensively in the art.

An alternative variant for the production of $CH_3OH$ is the reaction of $CO_2$ with $H_2$ so that the previous by-product $CO_2$ can be drawn upon also during the synthesis of this basic chemical. This reaction also produces $H_2O$ in addition to $CH_3OH$. Compared to the generation of methanol from syngas, the productivity when generating from $CO_2$ and $H_2$ is reduced by a factor of 3-10 because the water hinders the reaction. However, the yield can be increased with continuous removal of the water reaction product. This is achieved through the use of the membranes.

The membranes can be used in flexible geometry. The membranes allow water to be selectively separated under process conditions. Outfitted with a catalyst which is active for the chemical equilibrium reactions to be carried out, the yield can be increased significantly and the feed quality can be achieved more easily.

In an advantageous manner, water is selectively separated from the reaction even at high temperatures through a method according to the invention using organic membranes with hydrophobic surfaces. A utilized catalyst can be arranged on the membrane as bulk material, or a catalytically active membrane is used. The membrane is preferably used for converting carbon dioxide and hydrogen to methane (Sabatier reaction) or methanol.

The use according to the invention of the above-described membranes is utilized, for example, for separating water from the Sabatier reaction. To this end, a direct contact between water-separating membrane and catalyst is useful. The separation-active membrane can serve as a catalyst support. The catalyst or a catalyst precursor is arranged on the separation-active layer and activated as the case may be in suitable form, for example, through addition of heat. The activation of the catalyst is carried out, for example, under reaction conditions of the Sabatier reaction.

Further, the use according to the invention of the membranes described above allows an efficient implementation of a chemical equilibrium reaction in which methanol and water are obtained on the product side from carbon dioxide and hydrogen on the reactant side. The selective separation of water shifts the equilibrium in the product direction and promotes the formation of methanol.

DETAILED DESCRIPTION OF EXEMPLARY EMBODIMENTS

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description making apparent to those of skill in the art how the several forms of the present invention may be embodied in practice.

Embodiment examples for the method according to the invention are given in the following.

1. Reaction without membrane:

An alumina-supported nickel oxide, for example, the commercially available product METH 134, serves as catalyst. The catalyst was applied as bulk and correspondingly activated in a hydrogen/nitrogen stream (1:9). The reactant volume stream amounts to a total of approximately 250 Nl/h (liter per hour at STP). The $H_2/CO_2$ ratio is 4.1:1 (19.6 percent by volume $CO_2$, 80.4 percent by volume $H_2$) at a process pressure of 20 bar(g) (20 bars gauge) and reaction temperatures of 275° C. to 450° C. Conversions between 85% and 89% are achieved with a $CH_4$ selectivity of >99%. The $CH_4$ yield is likewise between 85% and 89%.

2. Reaction with membrane:

An alumina-supported nickel oxide, for example, the commercially available product METH 134 (manufactured by Clariant), serves as catalyst. The catalyst was applied as bulk and correspondingly activated in a hydrogen/nitrogen stream (1:9). The reactant volume stream amounts to a total of approximately 250 Nl/h. The $H_2/CO_2$ ratio is 4.1:1 (19.6 percent by volume $CO_2$, 80.4 percent by volume $H_2$) at a process pressure of 20 bar(g) and reaction temperatures of 240° C. to 450° C. The space velocity at the membrane is ~21.5 $s^{-1}$ or corresponds to a linear velocity of ~0.04 m/s. Conversions upward of 90% are achieved with a $CH_4$ selectivity of >99%. The $CH_4$ yield is likewise between >90%.

3. Reaction with membrane (catalyst-coated):

A coating of the membrane with nickel oxide is used as catalyst precursor. This precursor is reduced in a hydrogen/nitrogen stream (1:9) to the active metallic nickel and correspondingly activated. The reactant volume stream amounts to a total of approximately 1000 Nl/h. The $H_2/CO_2$ ratio is 4.1:1 (19.6 percent by volume $CO_2$, 80.4 percent by volume $H_2$) at a process pressure of 20 bar(g) and reaction temperatures of 240° C. to 450° C. The space velocity at the membrane is ~58 $s^{-1}$ or corresponds to a linear velocity of ~0.02 m/s. Conversions >95% are achieved with a $CH_4$ selectivity of >99%. The $CH_4$ yield is likewise greater than 95%.

Although the present invention has been described in detail on the basis of the exemplary embodiments, it is self-evident to a person skilled in the art that the invention is not restricted to these exemplary embodiments, but rather that modifications are possible in such a way that individual features may be omitted or other combinations of features presented may be implemented without departing from the scope of protection of the accompanying claims. The present invention comprises in particular all combinations of all of the individual features presented.

What is claimed is:

1. A method of carrying out a chemical equilibrium reaction in which carbon dioxide and hydrogen are converted, wherein the method comprises separating and removing from the reaction quantitative proportions of at least one product obtained in the reaction by using a permselective membrane made from a material having a porous structure with a mean pore size of less than 0.45 nm (4.5 Å), which material is hydrophobic at least on free surfaces thereof.

2. The method of claim 1, wherein the permselective membrane is a carbon membrane, the structure of the material is graphite-like and is formed by layers of the material, the structure is formed by at least one series of layers, which layers are arranged in planes, there is a mean spacing between adjacent layers of less than 0.45 nm (4.5 Å), and the series of layers is turbostratically disordered.

3. The method of claim 1, wherein at least one metal-containing catalyst is arranged on a surface of the permselective membrane.

4. The method of claim 3, wherein the at least one metal-containing catalyst comprises one or more of ruthenium, nickel, cobalt, rhodium, platinum, palladium, and alloys thereof.

5. The method of claim 1, wherein the chemical equilibrium reaction is carried out with a hydrogen surplus with respect to a stoichiometric use of molecular hydrogen.

6. The method of claim 5, wherein the hydrogen surplus amounts to 2.5% with respect to the stoichiometric use of molecular hydrogen.

7. The method of claim 1, wherein biogas, sewage gas, biomethane, molecular hydrogen-containing carbon dioxide streams, molecular hydrogen-releasing electrolysis, hydrogen streams or combinations thereof are used as sources of molecular hydrogen.

8. The method of claim 7, wherein the sources of molecular hydrogen are reduced and desulfurized and contain ≤1 ppm of oxygen ($O_2$) and sulfur (S).

9. The method of claim 1, wherein the equilibrium reaction is a Sabatier reaction.

10. The method of claim 9, wherein the Sabatier reaction is carried out at a pressure of from 1 to 100 bar and at a temperature of from 150 to 600° C.

11. The method of claim 10, wherein the Sabatier reaction is carried out at a pressure of from 10 to 20 bar and at a temperature of from 250 to 450° C.

12. The method of claim 11, wherein the Sabatier reaction is carried out at a pressure of about 20 bar and at a temperature of about 300° C.

13. The method of claim 1, wherein the equilibrium reaction is a methanol production reaction.

14. The method of claim 13, wherein the methanol production reaction is carried out at a pressure of from 80 bar up to and including 250 bar and at a temperature of from 150° C. up to and including 400° C.

15. The method of claim 2, wherein at east one metal-containing catalyst is arranged on a surface of the permselective membrane.

16. The method of claim 15, wherein the at least one metal-containing catalyst comprises one or more of ruthenium, nickel, cobalt, rhodium, platinum, palladium, and alloys thereof.

17. The method of claim 2, wherein the chemical equilibrium reaction is carried out with a hydrogen surplus with respect to a stoichiometric use of molecular hydrogen.

18. The method of claim 17, wherein the hydrogen surplus amounts to 2.5% with respect to the stoichiometric use of molecular hydrogen.

19. The method of claim 2, wherein biogas, sewage gas, biomethane, molecular hydrogen-containing carbon dioxide streams, molecular hydrogen-releasing electrolysis, hydrogen streams or combinations thereof are used as sources of molecular hydrogen.

20. The method of claim 19, wherein the sources of molecular hydrogen are reduced and desulfurized and contain ≤1 ppm of oxygen ($O_2$) and sulfur (S).

* * * * *